(12) United States Patent
Letizia et al.

(10) Patent No.: US 10,405,432 B2
(45) Date of Patent: Sep. 3, 2019

(54) STRETCHABLE ELECTRONICS FOR DENTISTRY APPLICATIONS AND METHOD OF MAKING THE SAME

(71) Applicants: Marco Letizia, Ecublens (CH); Pietro Maoddi, Bussigny (CH)

(72) Inventors: Marco Letizia, Ecublens (CH); Pietro Maoddi, Bussigny (CH)

(*) Notice: Subject to any disclaimer, the term of this patent is extended or adjusted under 35 U.S.C. 154(b) by 0 days.

(21) Appl. No.: 15/735,750

(22) PCT Filed: Jun. 22, 2016

(86) PCT No.: PCT/IB2016/053721
§ 371 (c)(1),
(2) Date: Dec. 12, 2017

(87) PCT Pub. No.: WO2017/001978
PCT Pub. Date: Jan. 5, 2017

(65) Prior Publication Data
US 2018/0168033 A1    Jun. 14, 2018

(30) Foreign Application Priority Data

Jun. 29, 2015  (WO) .................. PCT/IB2015/054881

(51) Int. Cl.
*H05K 3/14*    (2006.01)
*H05K 1/02*    (2006.01)
*A61C 19/05*   (2006.01)

(52) U.S. Cl.
CPC .......... *H05K 3/146* (2013.01); *H05K 1/0283* (2013.01); *A61C 19/05* (2013.01); *H05K 2201/0133* (2013.01)

(58) Field of Classification Search
CPC .......... H05K 3/14; H05K 3/143; H05K 3/146
See application file for complete search history.

(56) References Cited

U.S. PATENT DOCUMENTS

| 7,491,892 B2 | 2/2009 | Wagner et al. |
| 2004/0192082 A1 | 9/2004 | Wagner et al. |
| 2010/0238636 A1 | 9/2010 | Mascaro et al. |
| 2015/0131239 A1 | 5/2015 | Ha et al. |

FOREIGN PATENT DOCUMENTS

WO     2015061473 A1    4/2015

OTHER PUBLICATIONS

International Search Report; European Patent Office; International Application No. PCT/IB2016/053721; dated Oct. 7, 2016; 4 pages.

(Continued)

*Primary Examiner* — Jeremy C Norris
(74) *Attorney, Agent, or Firm* — Taft Stettinius & Hollister LLP (57) ABSTRACT

The present invention relates to a method for producing a stretchable conductor and/or electrical connection including providing a stretchable substrate, a liquid metal, a conductive metal and an adhesion material in a same evaporator chamber; depositing the liquid metal; depositing the adhesion material; depositing the conductive metal; wherein the liquid metal, the conductive metal and the adhesion material are deposited by evaporation; and the deposition by evaporation is made in vacuum.

12 Claims, 5 Drawing Sheets

(56) References Cited

OTHER PUBLICATIONS

Written Opinion of the International Searching Authority; European Patent Office; International Application No. PCT/IB2016/053721; dated Oct. 7, 2016; 6 pages.

J. William Boley et al.; Direct Writing on Gallium-Indium Alloy for Stretchable Electronics; Advanced Functional Materials; Jun. 18, 2014; pp. 3501-3507; vol. 24, Issue 23; Wiley Online Library; Copyright 1999-2016 John Wiley & Sons, Inc.

Aaron P. Gerratt et al.; Stretchable capacitive tactile skin on humanoid robot fingers—first experiments and results; 2014 14th IEEE-RAS International Conference on Humanoid Robots (Humanoids); Nov. 18-20, 2014; pp. 238-245; Madrid, Spain.

Jaewook Jeong et al.; Stretchable Low Resistance Thick Silver Electrode on Poly(dimethylsiloxane) Compliant Elastomeric Substrate; Japanese Journal of Applied Physics; 2010; 4 pages; vol. 49; Copyright 2010 The Japan Society of Applied Physics.

Ivan R. Minev et al.; Electronic dura mater for long-term multimodal neural interfaces; sciencemag.org; Jan. 9, 2015; pp. 159-163; vol. 347 Issue 6218.

Nicolas Tiercelin et al.; Polydimethylsiloxane membranes for millimeter-wave planar ultra flexible antennas; Institute of Physics Publishing; Journal of Micromechanics and Microengineering; 2006; pp. 2389-2395; vol. 16.

STRETCHABLE ELECTRONICS FOR DENTISTRY APPLICATIONS AND METHOD OF MAKING THE SAME

CROSS REFERENCE TO RELATED APPLICATIONS

This application is a U.S. national stage filing of International Patent Application No. PCT/IB2016/053721 filed on Jun. 22, 2016, which claims priority to International Patent Application No. PCT/IB2015/054881 filed on Jun. 29, 2015, the contents of each application hereby incorporated by reference in their entirety.

TECHNICAL FIELD

The present invention is in the field of electronics, stretchable electronics, thin film deposition and, in particular in the field of dentistry. Specifically, it concerns stretchable electronics and electrical transitions/connections onto stretchable substrates and flexible substrate used for electronics.

To fabricate stretchable electronics, two main processes are used: thin film metal deposition or patterning of liquid metal or conductive pastes on an elastic substrate.

In the case of the first process, thin film metal (e.g., Cr—Au) deposition on elastic substrates (e.g., Ecoflex, PDMS, polyurethane, silicones) are used to fabricate electrical connections that stretch and deform conformally to the substrate while remaining conductive and elastic (in a certain range of deformation). For such a purpose an adhesion layer (e.g. Cr, Ti) is deposited onto the elastic substrate to improve the adhesion forces between the substrate and a highly conductive metal (e.g. Au, Cu, Ag, Pt, Pd).

Depending on the substrate and the applications, deposition rates and metal thickness are different (U.S. Pat. No. 7,491,892 B2,). Lacour et al, Science 9, January 2015, Vol. 347 no. 6218 pp.; Gerratt et al., 2014 IEEE-RAS International Conference on Humanoid Robots, Madrid, 2014, pp. 238-24510 159-163 The thickness of the metallization is typically in the range from few atomic layers up to 100 nm, yielding a very thin circuit board.

Although the thin metal layer follows the elastic substrate deformation up to 20-25% of elongation and remains conductive (Lacour et al. and Gerratt et al), the metal connection is not conductive anymore at elongations larger than 20-25%. Upon a local stress (i.e. a pressure applied by a tip or a dental cusp), the electrical connection is locally interrupted, producing a failure of the device.

A transition of the conductive tracks from elastic substrates to traditional electronic substrates can be performed. For this purpose other materials at the interlace, such as conductive pastes and liquid metal alloys, are added to avoid excessive friction (rubbing and shearing) at the interface. However, the mechanical performances of this transition are poor and limit the ability of elongation to 5-10% (Lacour et al. and Gerratt et al).

Figure 1A:
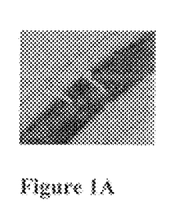
FIG. 1A shows the metal deposited onto the elastic substrate is damaged after being in contact with another object.

The mechanical contact between the deposited metal and the hard object is critical. Potential friction, rubbing or shearing at the interface damage the deposited metal pattern, thus reducing the working life of the connections. (see FIG. 1A). Soft material (e.g., conductive paste, conductive gel) has to be used to reduce rubbing and shearing at the interface of the transition. These conductive pastes or gels are typically harmful for humans. This limits the technological field wherein this technology may be applied. Furthermore, these conductive pastes or gels require a proper encapsulation, which is bulky and particularly increases the overall dimensions of the device.

Figure 1B:
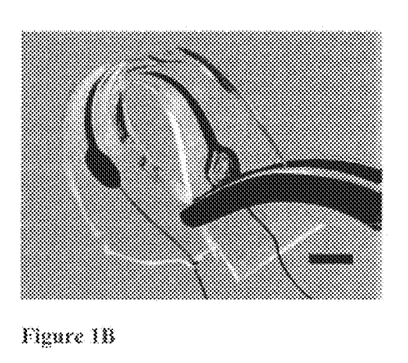
FIG. 1B shows the liquid metal encapsulated in elastic substrates.

In the case of the second process to fabricate electrical connections and circuits which stretch and deform conformally to the substrate while remaining conductive and elastic, liquid metals (typically eutectic GaIn or other Ga alloys) and conductive Ag-based pastes are used, (see FIG. 1B). These materials can be deposited with a syringe or a nozzle. In most cases, the pattern created with liquid metal or conductive pastes is encapsulated using silicones or other elastomers.

Said pattern fellows the elastic substrate deformation up to 80-150% of elongation and remains conductive (Tiercelin et al., Journal of Micromechanics and Microengineering, IOP Publishing, 2006, 16, pp. 2389-2395; Boley et al., Advanced Functional Materials 23, June 18, Vol. 24, pp. 3501-3507). The elastic deformation range and the conductive deformation range of the pattern of liquid metal or conductive pastes are higher than in the thin metal layer case but the conductivity of the electrical connection made with liquid metal is lower.

The use of conductive pastes, liquid metal alloys or other materials at the interface between two substrates allows performing transitions from elastic substrates and traditional electronic substrates. However, the mechanical performances of this transition are limited (5-10% of elongation). The electrical resistance per unit length of this type of connection is too high for many applications.

Moreover upon application of local stress (e.g. pressure applied by a dental cusp), the liquid metal is displaced and the connection interrupts producing a failure of the device.

The external surface of the liquid metal pattern may oxidize rapidly. Therefore, the transition between liquid metal lines and traditional electronics substrates requires a bulky encapsulation to avoid electrical failure.

The architecture of electric lines, pads, electrodes results bulky. Indeed, the metallization thickness typically is in the range from 50 to 800 μm and the conductors need to be further encapsulated by the elastic materials used as substrate. Thus, the overall thickness of the stretchable electronics board easily reaches 1 mm, which is inappropriate for many biomedical applications, such as dental occlusion assessment and implantable electrodes for electrical stimulation, where the thickness of the device has to be minimal (e.g. below 1 mm).

Nowadays, there is a real need for stretchable electronics and/or electronic connections which can stretch and deform conformally to the substrate, said electronics or connections remaining elastic and conductive and not presenting the drawbacks of the devices obtained by the two aforementioned processes: limitation of the ability of elongation and of the conductivity, limited transition between elastic substrates and traditional electronic substrates, bulky architecture and too high thickness, inclusion of harmful materials, high electrical resistance per unit length of connection. There is also a real need for a method which is more economic, more environment friendly and less complex.

SUMMARY OF THE INVENTION

The invention provides a solution to all the aforementioned drawbacks. The invention concerns a method for producing a stretchable conductor and/or electrical connection, a stretchable conductor and/or electrical connection being stretchable for more than 100% of the initial length depending on the deformation capacity of the stretchable substrate, a device comprising such a stretchable conductor and/or electrical connection as described throughout the present disclosure and the appended claims.

Figure 2A:
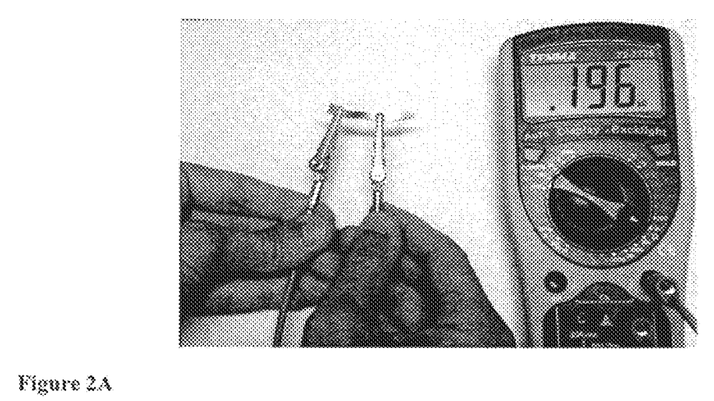
Figure 2B:
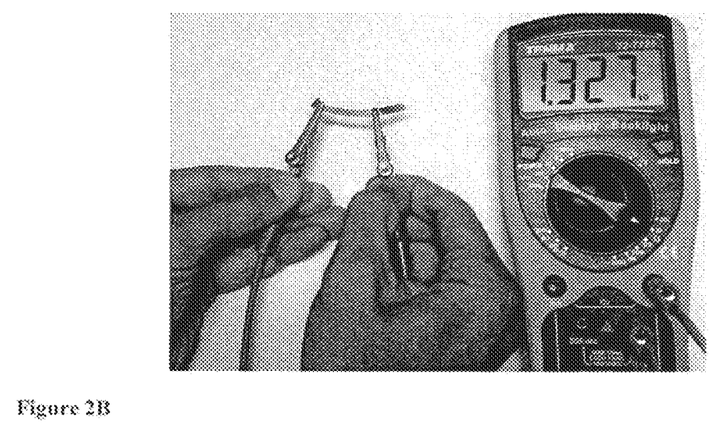

The inventors have found that the stretchable conductor and/or electrical connection obtained by the method of the invention and composed of thin metallic layers deposited onto elastic or stretchable substrates can deform for more than 300% of elongation, and up to 500% of elongation, while remaining conductive (see FIGS. 2A and 2B).

By using a stretchable conductor and/or electrical connection obtained with the method of the invention, the transition from the elastic substrate and the traditional electronic substrates does not need other materials at the interface, such as conductive paste. During the fabrication of the stretchable conductor and/or electrical connection, the continuous deposition of the liquid metal by evaporation during the whole process allows to combine said liquid metal with other materials, which improves the mechanical contact and the electrical connection at the transition from elastic substrate and traditional electronic substrates.

Moreover the metallization provided by the method or the process results in a very thin circuit board of a thickness in the range from a few microns to a few millimeters.

Accordingly, in an aspect, the invention provides a method for producing a stretchable conductor and/or electrical connection comprising
- providing a stretchable substrate, a liquid metal a conductive metal and an adhesion material in a same evaporator chamber;
- depositing the liquid metal;
- depositing the adhesion material;
- depositing the conductive metal;
- wherein
    - the liquid metal the conductive metal and the adhesion material are deposited by evaporation; and
    - the deposition by evaporation is made in vacuum.

In one embodiment the liquid metal is continuously deposited by evaporation during the whole process and the deposition of the adhesion material and conductive metal.

In another aspect, the invention provides a stretchable conductor and/or electrical connection, comprising a stretchable substrate, an adhesion material, a conductive metal and a liquid metal, wherein said adhesion material, said conductive metal and said liquid metal are under the term of layers.

In a further aspect, the invention provides a device comprising one or more stretchable conductors and/or electrical connections of the invention.

In one embodiment the device of the invention is selected from a strain gauge, a capacitive pad, a ground plane, a sensor, a capacitive sensor, a capacitive sensor array, an electronic mechanic connection.

In particular, in a further embodiment, the device of the invention is an electronic and mechanic connection comprising two circuits pads, wherein at least one of the pads are a stretchable conductor and/or electrical connection of the invention.

Further aspects and preferred embodiments of the invention are detailed herein below and in the appended claims. Further features and advantages of the invention will become apparent to the skilled person from the description of the preferred embodiments given below.

BRIEF DESCRIPTION OF THE DRAWINGS

FIG. 2 show an electrical strip patterned on PDMS at rest, namely at rest, (FIG. 2A) or under stretching (FIG. 2B).

FIG. 3 shows a schematic view of a thermal evaporator. Under vacuum, the electrical currents (5, 6, 7) flowing in thermal sources (2, 3, 4) heat up the materials to be evaporated. The vapors deposit these materials on the substrate above (1). By adjusting the current in the sources, the deposition rate changes. Multiple active sources are used at the same time.

FIG. 6 shows the transition between a classical printed circuit board (6) and a stretchable circuit (7) provided by the method of the invention. The stretchable circuit comprises an elastic substrate (4) on which conductive lines with pads (5) are patterned. The classical printed circuit board comprises a rigid or flexible board (1) on which conductive lines with pads (2) are patterned. The pads on the classical printed circuit board contain a slot in which an adhesive is present (3).

FIG. 8 shows a sample used for tensile stretching tests. A thin and narrow conductive line (2) is patterned with the method of the invention on a thin elastic substrate (1). The two extremities of the lines are connected to electric wires (3) using an adhesive on the top (4). Such sample is then stretched linearly using a computer-controlled machine in the direction depicted by the black arrows, while the electrical resistance of the line is measured.

DETAILED DESCRIPTION OF THE INVENTION

The present disclosure may be more readily understood by reference to the following detailed description presented in connection with the accompanying drawing figures, which form a part of this disclosure. It is to be understood that this disclosure is not limited to the specific conditions or parameters described and/or shown herein, and that the terminology used herein is for the purpose of describing particular embodiments by way of example only and is not intended to be limiting of the claimed disclosure.

As used herein adhesion material is a material that is used to improve the metal adhesion to the substrates.

As used herein conductive material is a metal that is solid at room conditions and presents the highest conductivity among the evaporated materials.

As used herein liquid metal is a metal material that is in a liquid or semi-liquid state up to a temperature of 90° C. and at atmospheric pressure condition.

As used herein, deposition rate means the amount of material deposited on the substrate per time unit, e.g. in a second.

As used herein, transition in the context of a connection means line, track of the electronic board and any conductive path between two regions or two components.

The invention relates to a method for producing a stretchable conductor and/or electrical connection comprising
  providing a stretchable substrate, a liquid metal, a conductive metal and an adhesion material in a same evaporator chamber;
  depositing the liquid metal;
  depositing the adhesion material;
  depositing the conductive metal;
  wherein
    the liquid metal, the conductive metal and the adhesion material are deposited by evaporation; and
    the deposition by evaporation is made in vacuum.

In particular, the invention relates to a method for producing a stretchable conductor and/or electrical connection comprising
  providing a stretchable substrate, a liquid metal, a conductive metal and an adhesion material in a same evaporator chamber;
  depositing the liquid metal onto the stretchable substrate;
  depositing the adhesion material;
  depositing the conductive metal;
  wherein
    the liquid metal, the conductive metal and the adhesion material are deposited by evaporation; and
    the deposition by evaporation is made in vacuum.

In one embodiment, the method of the invention further comprises a step of depositing the liquid metal onto the stretchable substrate and/or before depositing the adhesion material.

In one embodiment, the method of the invention further comprises a step of depositing the liquid metal onto the conductive metal and/or after depositing the conductive metal.

In one embodiments the liquid metal is successively, alternatively or continuously deposited.

In another embodiment, while depositing the adhesion material and/or the conductive metal, the liquid metal is not deposited or the liquid metal has a deposition rate of 0 nm/s.

In a further embodiment, the method of the invention further comprises a step of depositing the liquid metal after depositing the adhesion material and before depositing the conductive material.

In one embodiment, the liquid metal is continuously deposited by evaporation during the whole process and the depositions of the adhesion material and conductive metal.

In another embodiment, the liquid metal is successively deposited. While depositing the adhesion material and/or the conductive metal, the liquid metal is not deposited or the liquid metal has a deposition rate of 0 nm/s. The liquid metal is deposited before depositing the adhesion material and after depositing the conductive material.

Figure 4:
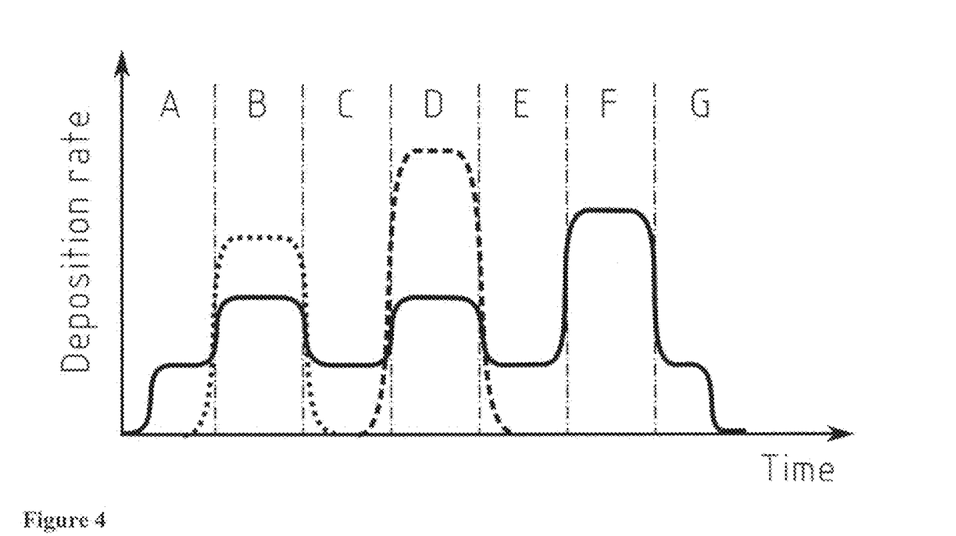
FIG. 4 shows a scheme of the deposition rate of the liquid metal, the adhesion material and the conductive metal during the method of the invention; the solid line represents the deposition rate (phases A to G) of the liquid metal, the dotted line represents the deposition rate of the adhesion material (phase B) and the dashed line represents the deposition rate of the conductive metal (phase D). Phase A: the liquid metal is deposited at a deposition rate >0 nm/s before depositing the adhesion material layer. Phase B: the deposition rate of the liquid metal is adjusted while the adhesion material layer is deposited. Phase C: the deposition of the adhesion material is stopped and the deposition rate of the liquid metal is adjusted. Phase D: the deposition rate of the liquid metal is adjusted while the conductive metal is deposited. Phase E: the deposition of the conductive metal is stopped and the deposition rate of the liquid metal is adjusted. Phase F: the deposition rate of the liquid metal is increased to obtain a final coating of liquid metal. Phase G: the deposition of the liquid metal is stopped.

In a further embodiment, in the method of the invention, the liquid metal, the conductive metal and the adhesion metal are deposited by evaporation at different deposition rates, which are variable during the process. The liquid metal may be deposited through the whole process of the production of the stretchable substrate and through all the steps of depositing the adhesion material and the conductive material (FIG. 4, phases A to G). The liquid metal may be deposited at variable or different deposition rates during die whole process.

Figure 3:
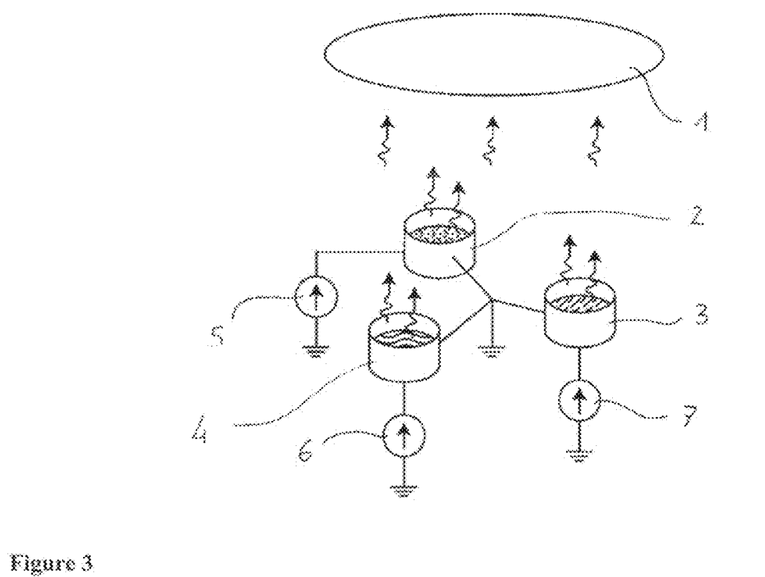

In particular, according to FIG. 3, the liquid metal placed in (4), the conductive metal placed in (2) and the adhesion material placed in (3) are deposited on the substrate (1) by evaporation at different deposition rates, which are variable during the process. The deposition rate of the liquid metal may be different from the deposition rate of the conductive metal and/or from the deposition rate of the adhesion material. The deposition rate of the liquid metal is different from the deposition rate of the conductive metal and/or from the deposition rate for the adhesion material, when the liquid metal is deposited together with the conductive metal and/or the adhesive material.

Since the evaporation temperatures of the metals and the material are depending on the pressure in the chamber and the type of material, the deposition rate of the metals and the material is controlled by adjusting the current in the sources (5, 6, 7) (see FIG. 3). The higher is the current, the higher is the evaporation rate. The currents may be in the range from 0 A to 500 A, 5 A to 500 A, 5 A to 70 A, or 50 A to 500 A. The deposition rates during the deposition process may be in the range from 0 to 12 Å/s (Ångstöm/second), or from 0 to 1.2 nm/s. The currents are preferably in the range from 0 A to 100 A. The deposition rates during the deposition process are preferably in the range from 0 to 3 nm/s. The temperatures of the sources may be in the range from 0° C. to 1500° C., or 0° C. to 200° C., and when the source is warmed up or heated, the temperatures of the heated sources may be in the range from 200° to 1500° C.

In another embodiment, the adhesion material and the conductive material are alternatively deposited by evaporation in the method of the invention. While depositing the adhesion material and/or the conductive metal, the liquid metal is not deposited or the liquid metal has a deposition rate of 0 nm/s. The liquid metal is deposited before depositing the adhesion material and after depositing said adhesion material, and before depositing the conductive material and after depositing said conductive material In a particular embodiment the adhesion material in the method of the invention is deposited before the conductive metal.

In another embodiment of the method of the invention, the liquid metal is deposited before depositing the adhesion material, while depositing said adhesion material, after depositing said adhesion material and before depositing the conductive material, while depositing said conductive material and after depositing said conductive material.

In a further embodiment of the method of the invention, the deposition by evaporation is made by a physical vapor deposition method selected from a deposition by sublimation process, cathodic arc deposition, electron beam physical vapor deposition, thermal evaporation, evaporative deposition, pulsed laser deposition, sputter deposition and/or from chemical vapor deposition, electron beam evaporation, thermal evaporation, electro-plating, molecular beam epitaxy.

According to another embodiment, preferably in the case of using thermal evaporation (see FIG. 3) as a deposition method, the method of the invention further comprises the following steps:
- positioning of the liquid metal, the conductive metal and the adhesion material on the different thermal sources (2, 3, 4) of the evaporator chamber;
- optionally adding an evaporation mask onto the stretchable substrates (1) to pattern the liquid metal, the adhesion material and the conductive metal in certain regions of the substrate,
- the thermal sources corresponding to the source onto which the liquid metal is placed, are progressively heated up until the liquid metal evaporates and deposits on the substrate;
- the thermal source corresponding to the source onto which the adhesion material is placed (3) is activated by adjusting the current flowing in the source (7) to have a deposition rate resulting in the deposition of a thin layer of material;
- the thermal source corresponding to the source onto which the adhesion material is placed (3), is turned off;
- the thermal source corresponding to the source onto which the conductive metal is placed (2), is activated by adjusting the current flowing in the source (5) to have a deposition rate resulting in the deposition of a thin layer of this metal;
- the thermal source corresponding to the source onto which the conductive metal is placed (2), is turned off;
- the current (6) continuously flowing into the sources corresponding onto which the liquid metal is placed (4), is increased to deposit the liquid metal under the form of a thin layer;
- the thermal source corresponding to the sources onto which the liquid metal is placed (4), is turned off.

Thin layer means a thickness of the layer after deposition of the metal or the material from 1 nm to 200 nm. To make stretchable conductors, the thickness of the adhesion material (e.g. Cr) is about 5 nm and the conductive material (e.g. Au) is about 30 nm.

The different metal layers resulted from the metallization in the method of the invention have an overall thickness of less than 100 nm or in the range from >0 nm to <100 nm, preferably from a few nanometers (>0 nm) to 100 nm, from 3 nm to 100 nm.

In a further embodiment of the method, the deposition of the metals and the material onto the stretchable substrate is patterned. Said pattern may be made through an evaporation mask and/or photolithography etching techniques.

In a further embodiment of the method of the invention, the stretchable substrate comprises an elastomeric material. The stretchable substrate or elastic substrate comprises elastomeric material. A non-exhaustive and non-limiting list of suitable stretchable and/or elastic materials according to the present invention comprises polymeric materials such as silicone (for example polydimethylsiloxane PDMS), stretchable or flexible polychlorobiphenyl, nitrile rubber, polyimide, latex, polyurethane, polyisoprene (synthetic rubber), any kind of elastomers, the Tango family of rubber-like materials (for example TangoPlus or FullCure930), polyurethane foam (foam rubber), XPS foam, polystyrene foam, phenolic foam, styrenic block copolymers, polyolefin blends, elastomeric alloys, thermoplastic polyurethanes (TPU), thermoplastic copolyester, thermoplastic polyamides and the like.

The stretchable conductor and/or electrical connection comprises electrically conductive material being any suitable material able to conduct the electrical current. Said material includes but is not limited to liquid metal and conductive metal.

The liquid metal is selected from metals including but not limiting to gallium, mercury as well as alloys thereof or oxides thereof. The liquid metal (e.g Ga alloys) or a metal with a low melting point (e.g. pure Ga) is combined with the adhesion material and the conductive metal during the evaporation to improve the mechanical property (elasticity and stretchability) of the stretchable conductor and/or electrical connection, said mechanical property is limited to the capacity of deformation of the elastomeric material used for the stretchable substrate.

The conductive metal is selected from metal including but not limiting to copper, silver, gold, aluminum, platinum, palladium and the like as well as alloys or oxides thereof. It allows creating an electrical connection with low resistance.

The adhesion material forms a layer and includes but is not limited to Cr, and Ti. It provides an adhesion between the stretchable substrate and the conductive metal.

In particular, in the method of the invention, the liquid metal is selected from gallium, mercury, chromium, alloys or oxides thereof and from metal being liquid or semi-liquid at less than 90° C. at atmospheric pressure condition; the adhesion material is metallic selected from Cr, Ti and the conductive material is metallic selected front Au, Ag, Cu or Au, Ag, Cu, Pt, Pd.

Figure 5:
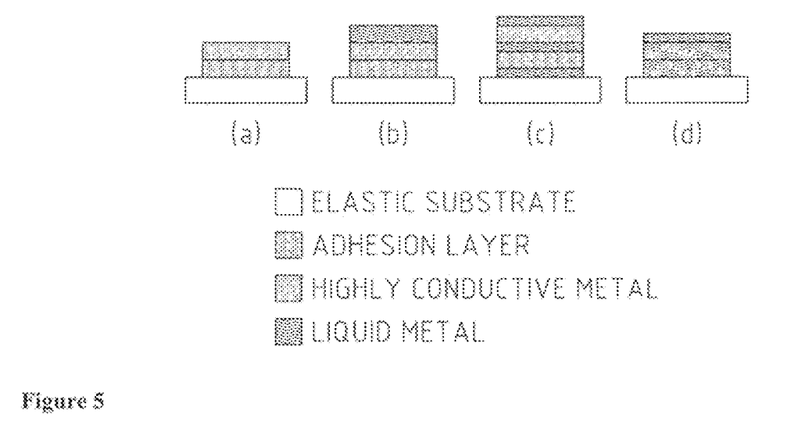
FIG. 5 shows example structures resulting from the deposition of thin metal on an elastic substrate; (a) traditional method: Cr is: deposited as an adhesion layer on PDMS (elastomeric material); Au guarantees good conduction; (b) liquid metal can be added on top of the Au layer; (c) liquid metal can be evaporated before or after the other materials in any order; (d) more complex structures with superior performance are obtained depending on the deposition rate and evaporating simultaneously the different metals and material.

According to the method of the invention, the adhesion material, the conductive metal and the liquid metal are evaporated in an evaporator chamber under vacuum. The liquid metal is evaporated before, during and after the other metal (conductive metal) and the adhesion material are evaporated. The deposition rate of the liquid metal changes during the process to ensure a proper layer adhesion and a proper combination between metals and materials. The vapor of the liquid metal in the chamber during the whole process combines with the other metal vapors before they deposit onto the substrate. At the end of the process, at room temperature and ambient conditions, the liquid metal is semi-liquid and combined with the other metals to ensure optimal mechanical and electrical properties for application in the stretchable electronics (see FIGS. 2 and 5).

In an aspect, the invention provides a stretchable conductor and/or electrical connection obtained by the method of the invention.

Since the deposition rates of the liquid metal are variable during the whole process, the method of the invention provides stretchable conductors and/or electrical connections, which may have different structures. Said structures include elastic or stretchable substrates forming a stretchable support onto which the adhesion material, the conductive material and the liquid metal are successively deposited (see FIG. 5b), elastic substrates onto which the liquid metal is alternatively deposited in any order between the adhesion and conductive layer (see FIG. 5c) and elastic substrates onto which the liquid metal is deposited continuously first with the adhesion material and then with the conductive material (see FIG. 5d).

The invention also provides a stretchable conductor and/or electrical connection comprises the stretchable substrate, an adhesion material, a conductive metal and a liquid metal, wherein said adhesion material, said conductive metal and said liquid metal are under the form of layers.

According to one embodiment, the stretchable conductor and/or electrical connection further comprises a liquid metal layer onto the stretchable substrate. This liquid metal layer may be optional. The stretchable substrate may be covered by a first liquid metal layer, if present, or directly by the adhesive layer, if said first liquid metal layer is absent.

According to a further embodiment, the stretchable conductor and/or electrical connection further comprises a liquid metal layer onto the conductive metal layer.

According to one embodiment, the adhesion material layer is covered by the conductive metal layer being covered by the liquid metal layer.

In a further embodiment, the adhesion material layer, the conductive metal layer and the liquid metal layer of the stretchable conductor and/or electrical connection are successive layers or alternating layers.

In one embodiment the stretchable conductor and/or electrical connection may further comprise a liquid metal layer between the adhesive material layer and the conductive metal layer.

In one embodiment, the stretchable conductor and/or electrical connection may comprise an adhesion material layer comprising liquid metal and adhesion material and a conductive metal layer comprising liquid metal and conductive metal.

In an embodiment, the stretchable conductor and/or electrical connection is stretchable for more than 100% of the initial length depending on the deformation capacity of the stretchable substrate. The deformation of the stretchable conductor and/or electrical connection is more than 300% of elongation, in the range from 100% to 500%, from 100% to 300% of the initial length. In a particular case, a stretchable conductor and/or electrical connection providing by the metallization of Cr—Au—Ga alloy stretches and remains conductive in the whole elastic range of 500% elongation of the substrate being PDMS.

In an aspect, the invention provides a device comprising one or more stretchable conductors and/or electrical connections according to the invention.

In one embodiment, the device of the invention is selected from a strain gauge, a capacitive pad, a ground plane, a sensor, a capacitive sensor, a capacitive sensor array, an electronic mechanic connection.

In a further embodiment, the device of the invention is for use in measuring dental occlusion and dental forces though capacitive means. Accordingly, the device for use in measuring dental occlusion of a subject through capacitive means, characterized in that it comprises: a substrate reversibly deformable upon dental occlusion; and a sensor incorporated within said substrate comprising at least one capacitive pad and transmission conductive lines, said transmission conductive lines operatively connecting the capacitive pad to a micro controller unit.

In another embodiment, the device of the invention is an electronic and mechanic connection comprising two circuit pads, wherein at least one of the pads is a stretchable conductor and/or electrical connection according to invention, namely obtained by the method of the invention.

The present invention is now illustrated by way of examples. These examples do not limit the scope this invention, which is defined by the appended claims.

EXAMPLES

Novel Transition from Stretchable to Flexible Electronics Circuit

Figure 6A:
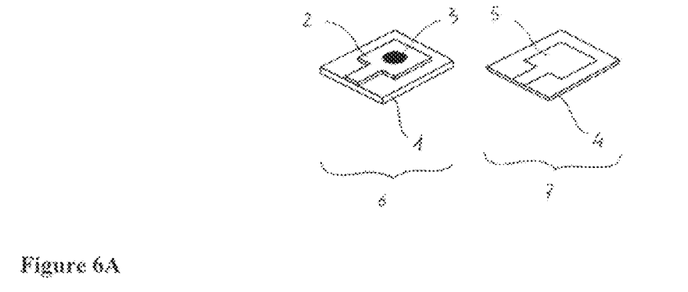
FIG. 6A shows a portion of classical printed circuit board and a portion of a stretchable circuit, to be put in mutual contact.
Figure 6B:
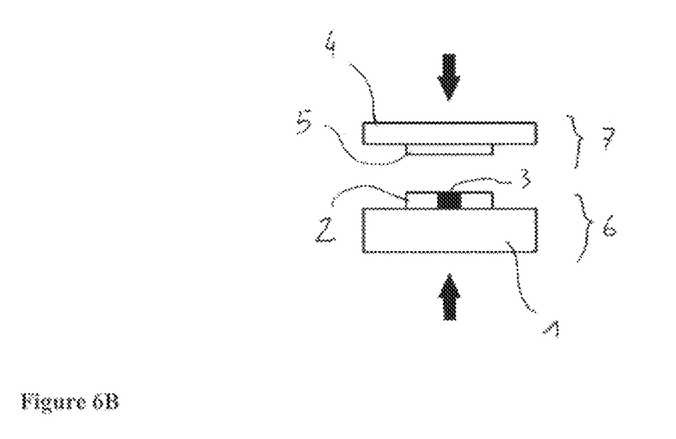
FIG. 6B represents a side cut view of the formation of the contact in the transition between the classical printed circuit board and the stretchable circuit.

The method of the invention resulting into deposited metals on elastic substrates allows to put in electrical contact the flexible electronic board to the stretchable one (see FIG. 6). The liquid metal evaporated and combined with Au can remain in contact with the flexible electronic metal parts.

A pad (2, 5) is patterned on both the flexible substrate (1) and the stretchable one (4) to increase the contact region of the two circuits. A pattern is created in the flexible board with photolithography and etching techniques. In this region an adhesive is placed (3) to improve the adhesion between the two substrates (see FIG. 6A). The amount of this adhesive is below the level of the metallization, pulling the stretchable PCB (6) towards the flexible one (7), improving the electrical contact (see FIG. 6B). Further encapsulation and mechanical clumps can be added in this region to improve the adhesion.

Figure 8:
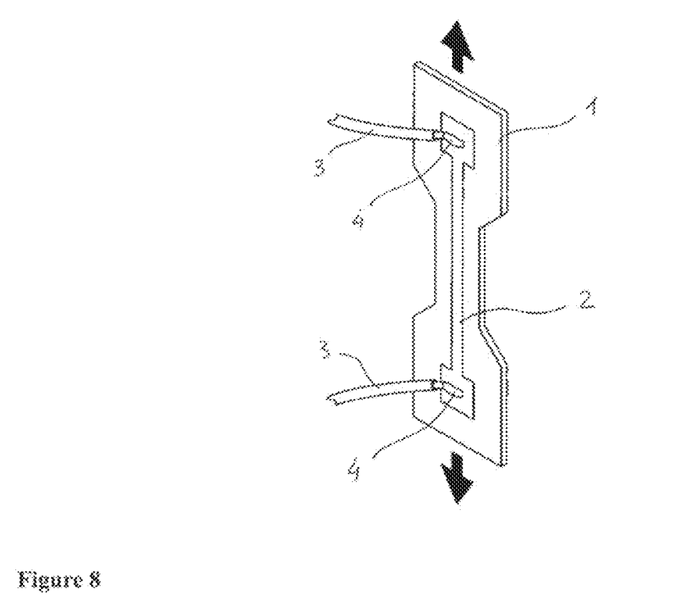
Figure 9:
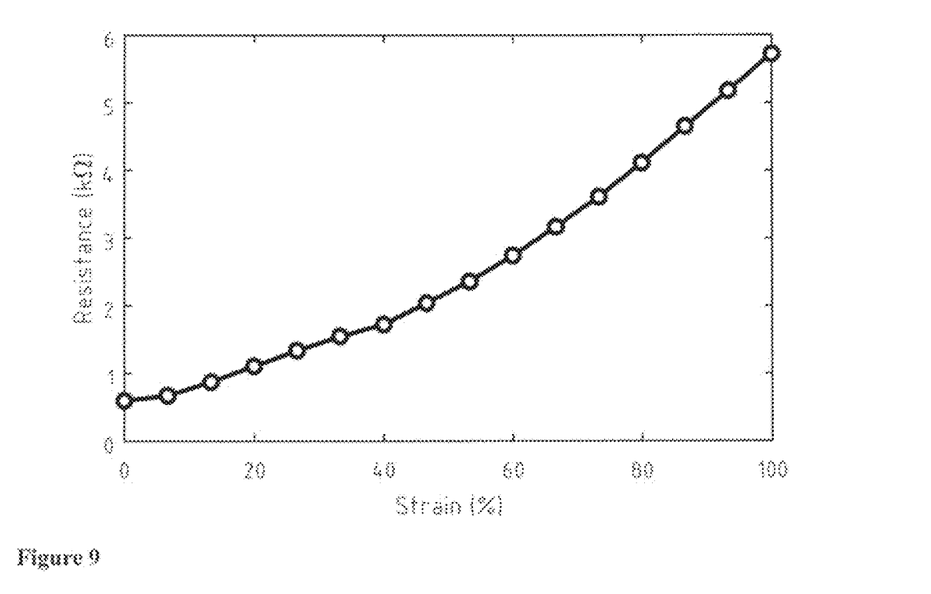
FIG. 9 shows an example measurement of the electrical resistance for various mechanical elongations of a sample prepared as in FIG. 8.

Using the method of invention, a sample for mechanical stretching tests was prepared (see FIG. 8). The sample consists of a narrow conductive line (2) was patterned on thin silicone (1). Such a line has 5 cm length and 250 µm width at rest. The metal deposition was performed by evaporating Cr, Au and Ga at a rate of 1 nm/s, 3 nm/s and 0.1 nm/s respectively. The deposition of the Ga occurred along the entire process. Electrical wires (3) are directly connected to the pads on the sample using an adhesive (4). The sample was then tested. A computer-controlled mechanical test machine linearly extended the sample (as indicated by the arrows in FIG. 6) and the resistance of the line for different values of strain was measured (see FIG. 9). The line remains electrically conductive up to 100% of strain and more.

Application in Dentistry

The method of the invention also allows the use of stretchable electronics in fields of technological application where the stress and deformation of the substrate are much higher than the current state of the art. Furthermore, this invention introduces the possibility of interlacing stretchable electronics substrates with traditional electronic substrates without using harmful conductive pastes and other liquid conductors allowing stretchable electronics to be used in fields of application where toxicity is forbidden (e.g. the dental or medical field).

Figure 7A:
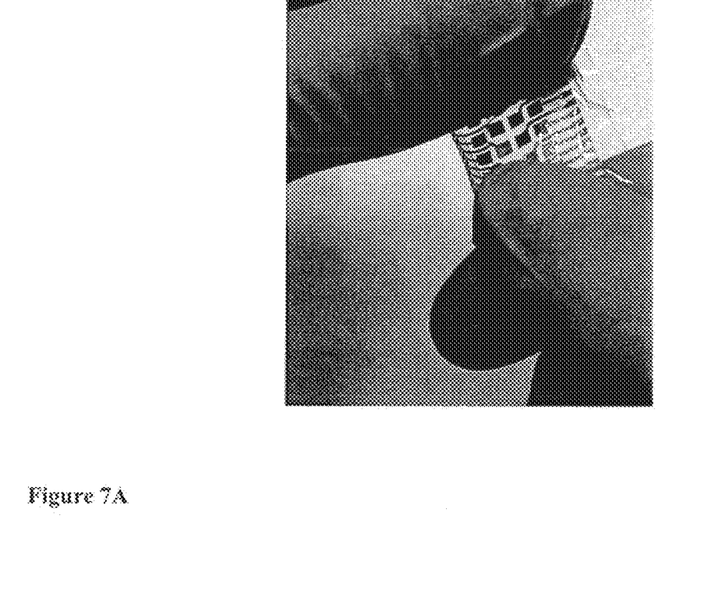
FIG. 7A shows a stretchable capacitive array patterned on PDMS.
Figure 7B:
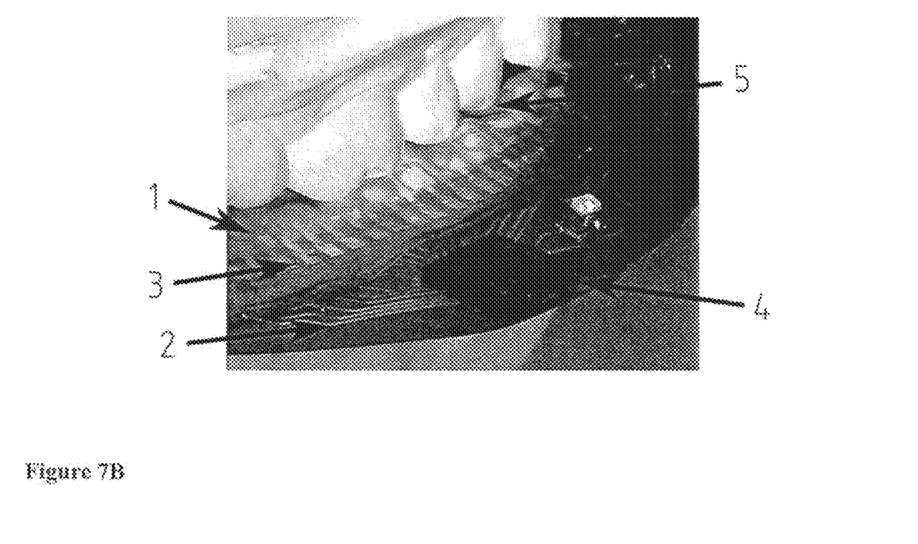
FIG. 7B shows an array of stretchable capacitive pressure sensors patterned on PDMS (1). A transition (3) formed using the method of the invention is used to provide the electrical connections to a flexible PCB (2). The electronics on the flexible PCB (4) read the signals from the sensor array and evaluate the distribution of the forces applied on the sensors by dental cusps (5).

Using the method of invention, a pressure sensitive capacitive sensor array on biomedical silicone have been fabricated (FIG. 7A). The sensor array (1) has been connected (3) to a semi-rigid electronic board (2) without using any conductive pastes or harmful materials (FIG. 7B). The electronics on the board (4) processes the signals gathered by the sensor array and evaluates the patient occlusion. Upon dental forces and stresses (5), the electronics elements adapt their shape to the dental topology, stretches, compresses and relaxes while remaining conductive and elastic even for high deformations.

REFERENCES

[1] U.S. Pat. No 7,491,892 B2—Stretchable and elastic interconnects, Princeton University

[2] S. P. Lacour et al, Electronic dura mater for long term multimodal neural interfaces, Science 9, January 2015, Vol. 347 no. 6218 pp. 159-163

[3] A. P. Gerratt, N. Sommer, S. P. Lacour and A. Billard, Stretchable capacitive tactile skin on humanoid robot fingers—First experiments and results, 2014 IEEE-RAS International Conference on Humanoid Robots, Madrid, 2014, pp. 238-24510

[4] N. Tiercelin, P. Coquet, R. Sauleau, V. Senez and H. Fujita, Polydimethylsiloxane membranes for millimeter wave planar ultra flexible antennas, Journal of Micromechanics and Microengineering, IOP Publishing, 2006, pp. 2389-2395

[5] J. W. Boley, E. L. White, G. T.-C. Chiu, R. K. Kramer, Direct Writing of Gallium-Indium Alloy for Stretchable Electronics, Advanced Functional Materials 23, June 18, Vol. 24, pp. 3501-3507.

The invention claimed is:

1. A method for producing a stretchable conductor and/or electrical connection comprising
providing a stretchable substrate, a liquid metal, a conductive metal and an adhesion material in a same evaporator chamber;
depositing the liquid metal;
depositing the adhesion material;
depositing the conductive metal;
wherein
the liquid metal, the conductive metal and the adhesion material are deposited by evaporation in vacuum;
the liquid metal, the conductive metal and the adhesion material are deposited at different deposition rates, which are variable during the process; and
said adhesion material, said conductive metal and said liquid metal are deposited under the form of layers or combine each other to form a conductive layer on the stretchable substrate.

2. The method according to claim 1, wherein the adhesion material is deposited before the conductive metal.

3. The method according to claim 1 further comprising a step of depositing the liquid metal onto the stretchable substrate and/or before depositing the adhesion material.

4. The method according to claim 1, wherein the liquid metal is successively, alternatively or continuously deposited.

5. The method according to claim 1, wherein the liquid metal has a deposition rate of 0 nm/s while depositing the adhesion material and the conductive metal.

6. The method according to claim 1 further comprising a step of depositing the liquid metal after depositing the adhesion material and before depositing the conductive material.

7. The method according to claim 1, wherein the liquid metal is continuously deposited by evaporation during the whole process and the deposition of the adhesion material and conductive metal.

8. The method according to claim 1, wherein the liquid metal is deposited before depositing the adhesion material, during depositing said adhesion material, after depositing said adhesion material and before depositing the conductive material, during depositing said conductive material and after depositing said conductive material.

9. The method according to claim 1, wherein the deposition by evaporation is made by a physical vapor deposition method selected from a deposition by sublimation process, cathodic arc deposition, electron beam physical vapor deposition, thermal evaporation, evaporative deposition, pulse laser deposition, sputter deposition and/or from chemical vapor deposition, electron beam evaporation, thermal evaporation, electro-plating, molecular beam epitaxy.

10. The method according to claim 1, wherein the stretchable substrate comprises an elastomeric material.

11. The method according to claim 1, wherein the liquid metal is selected from gallium, mercury, chromium, alloys or oxides thereof and from metal being liquid or semi-liquid at 90° C. at atmospheric pressure condition; and the adhesion material is metallic selected from Cr, Ti and the conductive material is metallic selected from Au, Ag, Cu, Pt, Pd.

12. The method according to claim 1, wherein the deposition of the metals and the material onto the stretchable substrate is patterned.

* * * * *

UNITED STATES PATENT AND TRADEMARK OFFICE
CERTIFICATE OF CORRECTION

| | | |
|---|---|---|
| PATENT NO. | : 10,405,432 B2 | Page 1 of 1 |
| APPLICATION NO. | : 15/735750 | |
| DATED | : September 3, 2019 | |
| INVENTOR(S) | : Marco Letizia et al. | |

It is certified that error appears in the above-identified patent and that said Letters Patent is hereby corrected as shown below:

In the Specification

Column 3
- Line 43: "... the term of layers ..." to be replaced with "... the form of layers ..."

Column 10
- Line 46: "... the possibility of interlacing stretchable ..." to be replaced with "... the possibility of interfacing stretchable ..."

Signed and Sealed this
Eighth Day of October, 2019

Andrei Iancu
*Director of the United States Patent and Trademark Office*